(12) United States Patent
Roos

(10) Patent No.: US 8,617,537 B2
(45) Date of Patent: Dec. 31, 2013

(54) **CONTROLLED ACTIVATION OF THE REUTERIN-PRODUCTION MACHINERY OF *LACTOBACILLUS***

(75) Inventor: Stefan Roos, Uppsala (SE)

(73) Assignee: Biogaia AB, Stockholm (SE)

( * ) Notice: Subject to any disclaimer, the term of this patent is extended or adjusted under 35 U.S.C. 154(b) by 547 days.

(21) Appl. No.: 12/481,530

(22) Filed: Jun. 9, 2009

(65) Prior Publication Data

US 2009/0304656 A1  Dec. 10, 2009

Related U.S. Application Data

(60) Provisional application No. 61/131,608, filed on Jun. 10, 2008.

(51) Int. Cl.
*A61K 35/74* (2006.01)

(52) U.S. Cl.
USPC .................................. 424/93.45; 435/252.9

(58) Field of Classification Search
None
See application file for complete search history.

(56) References Cited

U.S. PATENT DOCUMENTS

| | | |
|---|---|---|
| 5,439,678 A | 8/1995 | Dobrogosz et al. |
| 5,458,875 A | 10/1995 | Casas-Perez et al. |
| 5,534,253 A | 7/1996 | Casas et al. |
| 5,837,238 A | 11/1998 | Casas et al. |
| 5,849,289 A | 12/1998 | Dobrogosz et al. |

OTHER PUBLICATIONS

Arqués et al., International Journal of Food Microbiology, 2004, vol. 95, p. 225-229.*
Doleyers et al., Appl. Microbiol. Biotechnol., 2005, vol. 68, p. 467-474.*
Morgan et al., Journal of Microbiological Methods, 2006, vol. 66, p. 183-193.*
Vollenweider et al., Appl. Microbiol. Biotechnol., 2004, vol. 64, p. 16-27.*
Sriramulu, et al., *Lactobacillus reuteri* DSM 20016 Produces Cobalamin-Dependent Diol Dehydratase in Metabolosomes and Metabolizes 1,2-Propanediol by Disproportionation; Journal of Bacteriology, Jul. 2008; p. 4559-4567; vol. 190, No. 13.

* cited by examiner

*Primary Examiner* — Kade Ariani
(74) *Attorney, Agent, or Firm* — Lynn E. Barber

(57) ABSTRACT

Methods for the controlled activation of the reuterin-production machinery of *Lactobacillus reuteri* by adding glycerol and other substances during the manufacture of cell-cultures and keeping the produced reuterin in the bacterial cell during preservation and storage. In particular this invention relates to the manufacture of large amounts of *L. reuteri* that are loaded with reuterin, and the use of such loaded bacteria for applications such as prevention and treatment of diseases, for food applications and the like.

12 Claims, 9 Drawing Sheets

Figure 1:
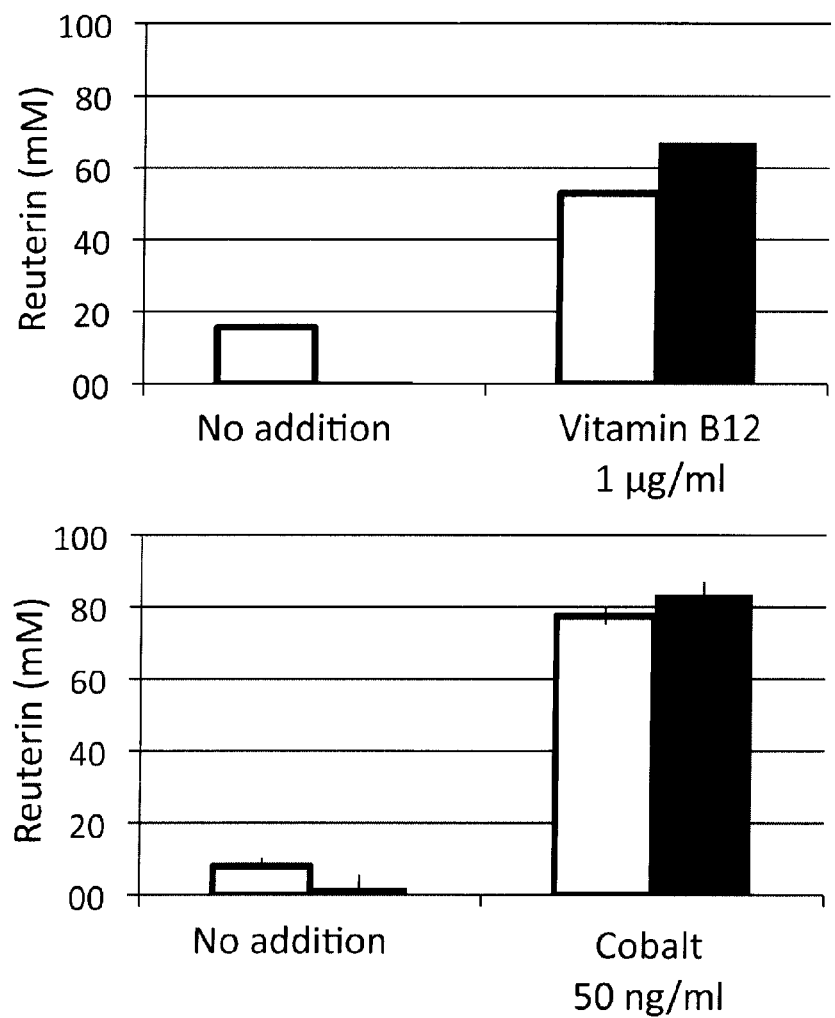

A.

B.

C.

D.

E.

F.

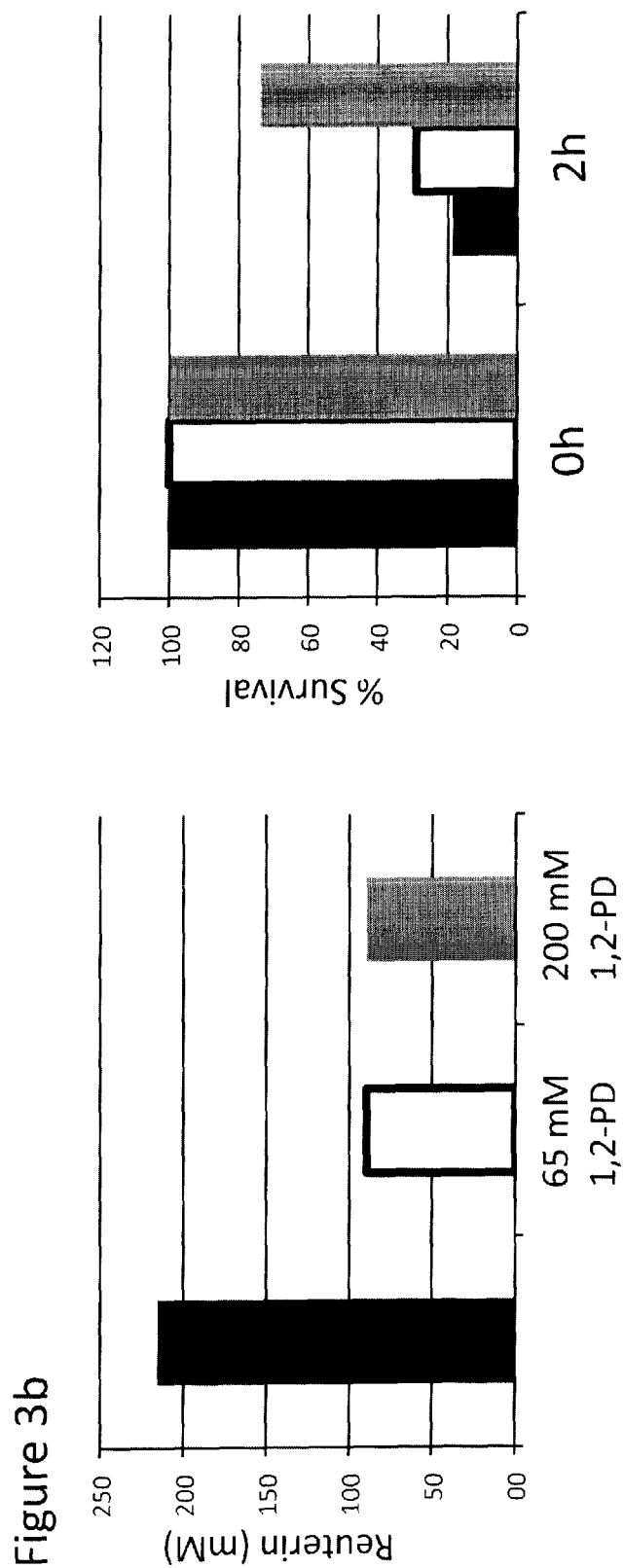

A.

B.

US 8,617,537 B2

CONTROLLED ACTIVATION OF THE REUTERIN-PRODUCTION MACHINERY OF *LACTOBACILLUS*

CROSS-REFERENCE TO RELATED APPLICATIONS

This application claims priority to U.S. Provisional Patent Application No. 61/131,608 having a filing date of Jun. 10, 2008, which is hereby incorporated by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO SEQUENCE LISTING

Not applicable.

BACKGROUND OF THE INVENTION

The invention relates to the controlled activation of the reuterin-production machinery of *Lactobacillus reuteri* by adding glycerol and other substances during the manufacture of cell-cultures and keeping the produced reuterin in the bacterial cell during preservation and storage. In particular this invention relates to the manufacture of large amounts of *L. reuteri* that are loaded with reuterin, and the use of such loaded bacteria for applications such as prevention and treatment of diseases, for food applications and the like.

DESCRIPTION OF THE PRIOR ART

Cells of prokaryotes have been viewed as primitive, although some contain unusual enclosures known as microcompartments (MCS), which appear to serve as primitive organelles inside bacterial cells. The carboxysome (which is involved in fixing carbon dioxide) was for nearly 30 years the only microcompartment recognized within microbial cells.

In 2005, professor Todd O. Yeates and his colleagues revealed the first structural details of bacterial microcompartments. The first high-resolution structures of the bacterial microcompartment proteins reveal principles of construction highly similar to those seen in some viruses. Six identical protein subunits come together to form a hexameric unit, which constitutes the building block for the shell. These hexameric units pack tightly together to form a molecular layer that contains only tiny pores. This tight packing appears to restrict movement of molecules into and out of the microcompartment, except through the pores.

Cluster analysis of homologues of microbial microcompartment-specific proteins suggests that such enclosures could be involved in as many as seven different metabolic processes in various bacterial species (Thomas A. Bobik. 2007. Bacterial Microcompartments. Microbe. 1:25-31.). The building blocks of bacterial microcompartments are exclusively proteins and glycoproteins. Electron microscopy (required to observe microcompartments) shows no lipid monolayer or bilayer (as in vesicles of the eukaryotes) surrounding such microcompartments, making them the only known protein-based metabolic compartments in living cells. Members of bacterial genera, including *Salmonella, Escherichia, Klebsiella, Clostridium, Fusobacterium, Shigella, Listeria*, and *Yersinia*, contain the components needed for degrading 1,2-propanediol (1,2-PD) or ethanolamine in their microcompartments (1). Another property of microcompartments is thought to be their ability to act as containers for substrates toxic for the bacteria itself, as in the case of *L. reuteri* the antimicrobial reuterin. GenBank searches, by Bobik, for microcompartment shell genes, showed that about 25% (85 of 337) of bacterial genomes contain shell gene homologues. In most of those 25% of bacterial genomes that carry those homologue genes, the shell genes cluster with other genes encoding microcompartment-associated enzymes. It is shown that the genes coding for reuterin production and the genes coding for the microcompartment structures are adjacent.

In May 2008, Sriramulu et al. (Sriramulu D D, Liang M, Hernandez-Romero D, Raux-Deery E, Lunsdorf H, Parsons J B, Warren M J, Prentice M B: *Lactobacillus reuteri* DSM 20016 produces cobalamin-dependent diol dehydratase in metabolosomes and metabolizes 1,2-propanediol by disproportionation. *J Bacteriol* 2008, 190(13):4559-4567) presented the first demonstration that the antimicrobial agent-producing organism *Lactobacillus reuteri* has the capacity to synthesize a bacterial microcompartment (carboxysome or metabolosome) when grown on modified MRS media containing 65 mM 1,2-propanediol (PD) and low amounts of glucose. The organism produced a cobalamin-dependent diol dehydratase enzyme induced by 1,2-PD. Linked cobalamin synthesis and pdu (propanediol utilization) operons were present in the *L. reuteri* DSM 20016 genome sequence, and the entire pdu operon was amplified from a laboratory strain of *L. reuteri* DSM 20016 by PCR, confirming its presence in the propanediol metabolizing organism. However growth in a modified MRS-media, with 65 mM 1,2-PD and low amounts of glucose, is not applicable in an industrial setting due to the very low growth rate of the bacteria in this media. Unlike the invention herein they do not describe the addition of glycerol during the manufacture of cell cultures making it possible to load the microcompartments with reuterin.

*Lactobacillus reuteri* is a bacterium known to produce the antimicrobial substance 3-hydroxypropionaldehyde (HPA), also called reuterin. Reuterin's antibacterial activity is described in for example U.S. Pat. Nos. 5,439,678; 5,458,875; 5,534,253; 5,837,238; and 5,849,289. Reuterin is a low molecular weight, neutral, water soluble compound capable of inhibiting growth of species representing all bacterial genera tested thus far, including: *Escherichia, Salmonella, Shigella, Proteus, Pseudomonas, Clostridium, Staphylococcus, Streptococcus*, and *Helicobacter pylori*; and also several fungi and other microorganisms. When glycerol is used as external electron acceptor is thus transformed to 1,3 propanediol, reuterin is produced as an intermediate. This reaction is completed when coupled to the fermentation of sugars such as glucose.

Production of reuterin is dependant on a complex machinery involving: the enzyme glycerol/diol dehydratase catalyzing the reaction; cobalamin (vitamin B12), a cofactor of the enzyme, which is synthesized via an intricate pathway; factors used for regeneration of the enzyme; and microcompartment structures more than 100 nm across and formed by polypeptides. All this together involves more than 50 genes that are induced when they are needed. The additions of 1,2-PD or glycerol to the growth media prime the production of large amounts of microcompartment structures. Adding glycerol at a later stage to the bacterial culture results in production of reuterin. The reuterin is loaded, stored and preserved within the microcompartments until they are ready to release the substance. Without any growth and substrate (including glycerol), when applying L. reuteri in its normal condition (without fully loaded microcompartments), for example on the skin, there would normally be no release of reuterin. So it was a surprise that the L. reuteri activated and with reuterin preserved in the microcompartments according to the invention herein successfully and fast released reuterin in inhospitable environments, like the skin of a human, on foods or other similar locations and of course also in more traditional application areas for probiotics such as the GI- and GU-tract, mouth and nose of animals including humans.

The proliferation of skin pathogens such as *Staphylococcus aureus, Streptococcus pyogenes* or *Propionibacterium acnes*, or of certain yeasts, can lead to infected wounds and to dysregulation of the cutaneous system, or even more serious disorders of skin or of mucous membranes, such as eczema, candidiases, dermatitises, impetigo, etc. Many means of treatment against these pathogenic agents are known. The most conventionally used are antibiotics or chemical antibacterial agents. They are, for example, compositions based on aldehydes and derivatives.

Another skin disease where the treatment involves both oral and/or topical antibiotics is Rosacea, affecting the middle third of the face, causing persistent redness over the areas of the face and nose that normally blush.

Infections caused by methicillin-resistant *Staphylococcus aureus* (MRSA) and related gram-positive pathogens are a growing medical concern. These include MRSA, methicillin resistant *Staphylococcus epidermidis* (MRSE), and methicillin resistant coagulase negative *Staphylococci* (MRCNS). Vancomycin, a glycopeptide antibiotic, is currently the agent of choice for combating these infections. With the increased usage of Vancomycin, the emergence of resistant stains of vancomycin-resistant *Staphylococci* (VRSA) was as expected a fact. Thus there is an increasing need for agents effective against such pathogens (MRSA/VRSA) that are at the same time free from undesirable side effects.

*S. aureus* most commonly colonizes the nostrils, although the respiratory tract, opened wounds, intravenous catheters, and urinary tract are also potential sites for infection. Healthy individuals may carry MRSA asymptomatically for periods ranging from a few weeks to many years.

Another example of a skin disorder which may be difficult to treat and which has a variety of causes is contact dermatitis, which may be triggered in sensitive subjects by skin contact with an external stimulus/agent.

Using *Lactobacillus* for treatment of skin disorders is already known in the art, it is for example described in U.S. Pat. Application No. 05/201996. The invention relates to the field of skin disorder prevention and/or treatment, using the formulations containing probiotic bacteria, such as *Lactobacillus fermentum* VRI-002 strain. The administration route is preferably oral.

Other bacterial agents, such as the *Bacillus*, can also be used on skin or mucous membranes. Specifically, in application WO 98/47374, strains of *Bacillus* are used in compositions intended to prevent bacterial, viral or fungal infections of skin.

However, the problem with treatments with lactobacilli, topically or in other inhospitable environments, using other bacteria described in the prior art is the short lifetime of the bacteria due to the inhospitable environment of the skin or elsewhere. This is solved by the invention herein by administering the L. reuteri with loaded microcompartments in the "stand by" mode for secreting reuterin. Thus the L. reuteri accomplish secretion of reuterin before they die off.

BRIEF SUMMARY OF THE INVENTION

The present invention pertains to the method of controlling the activation of the reuterin-production machinery of L. reuteri by priming the reuterin producing machinery with 1.2 PD or glycerol and later in the manufacturing process of cell-cultures adding glycerol to the bacterial culture, at a certain point before preservation. The present invention also relates to the addition of vitamin B12, cobalt and Vitamin C to the growth media for improving the conditions for optimal growth and production of microcompartments and reuterin of L. reuteri bacteria during the manufacturing process.

In particular this invention relates to the manufacture of large amounts of L. reuteri cells that are loaded with reuterin and the use of such prepared bacteria in compositions for example in prevention and treatment of diseases and food compositions. More specifically these compositions are intended to be administered to humans, for example topically for the purpose of preventing or treating disorders induced by pathogens of the cutaneous system. These compositions can also be used for nasal application for the treatment of MRSA. The invention circumvents the need for growth and survival of the L. reuteri bacteria in in-hospitable environments.

In this respect, before explaining some embodiments of the invention in detail, it is to be understood that the invention is not limited in its application to the details of construction and to the arrangements of the components set forth in the following descriptions or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTIONS OF THE DRAWINGS

FIG. 1. Are graphs illustrating the effects of reuterin levels in supernatant from strains DSM 17938 (empty bars) and MM4-1A (black bars) grown to stationary phase in B12-media with or without vitamin B12 (top) or cobalt (bottom).

Figure 2:
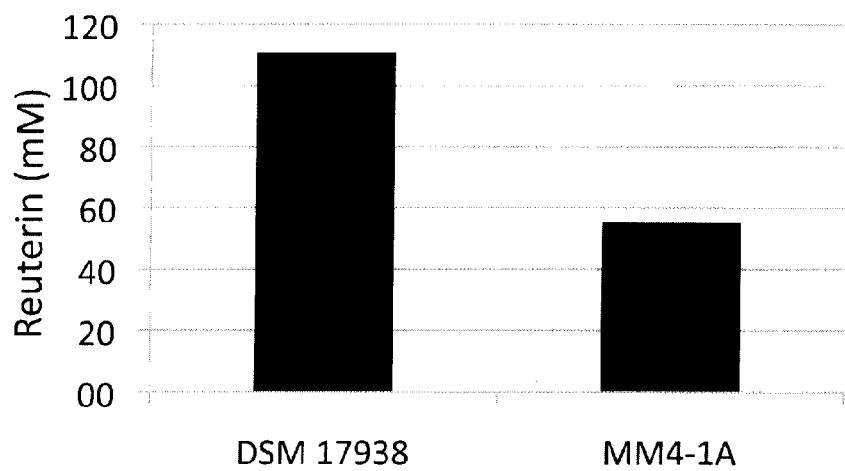

FIG. 2. Is a graph illustrating the effect of levels from supernatants of strains DSM 17938 and MM4-1A grown to stationary phase in MRS-media.

Figure 3A:
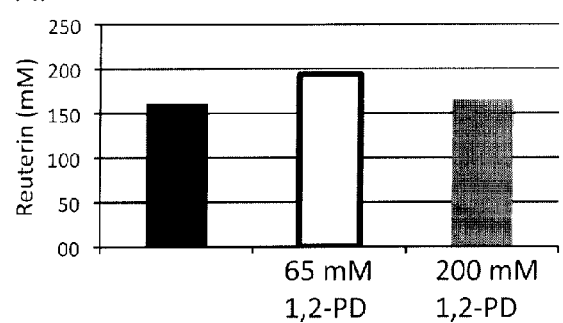
Figure 3A:
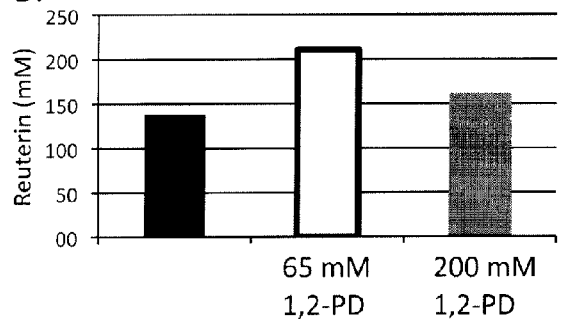
Figure 3A:
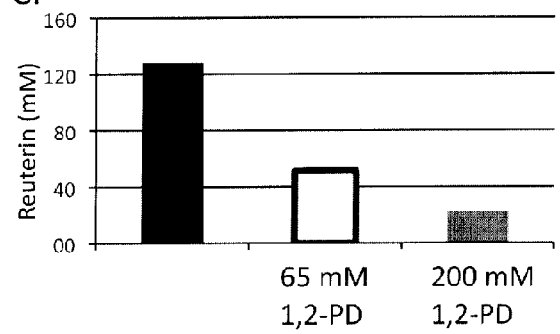
Figure 3A:
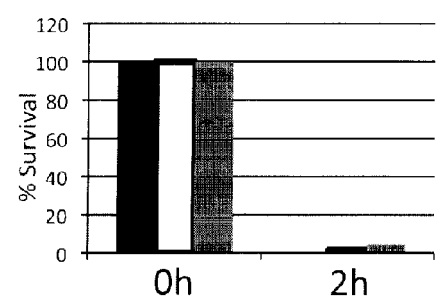
Figure 3A:
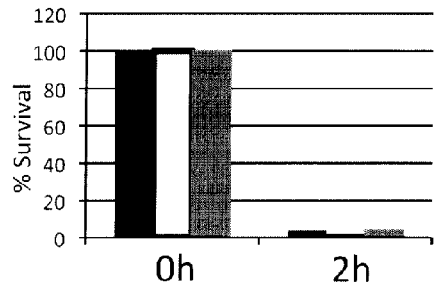
Figure 3A:
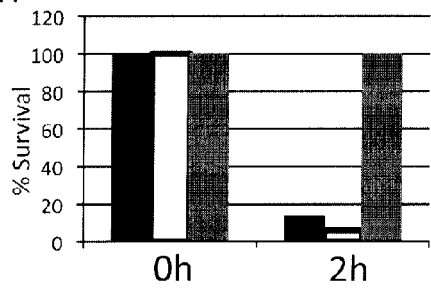

FIG. 3a. Is a graph illustrating the effect of addition of 1,2-PD on reuterin levels in supernatant and survival of strain MM4-1A grown to stationary phase in MRS with (A, D) no addition of cobalt, vitamin B12 (B, E), 50 ng/ml cobalt (C, F), 1 µg/ml vitamin B12. Black bars indicate no addition of 1,2-PD. White bars indicate 65 mM addition of 1,2-PD. Grey bars indicate 200 mM addition of 1,2-PD. Survival was measured before (0 h) and after (2 h) of incubation of cells in 200 mM glycerol/water solution.

FIG. 3b. Is a graph illustrating the effect of the addition of 1,2-PD on reuterin levels in supernatant and survival of strain DSM 17938 grown to stationary phase in B12-media with addition of 1 µg/ml vitamin B12. Black bars indicate no addition of 1,2-PD. White bars indicate 65 mM addition of 1,2-PD. Grey bars indicate 200 mM addition of 1,2-PD. Survival was measured before (0 h) and after (2 h) of incubation of cells in 200 mM glycerol/water solution.

Figure 4:
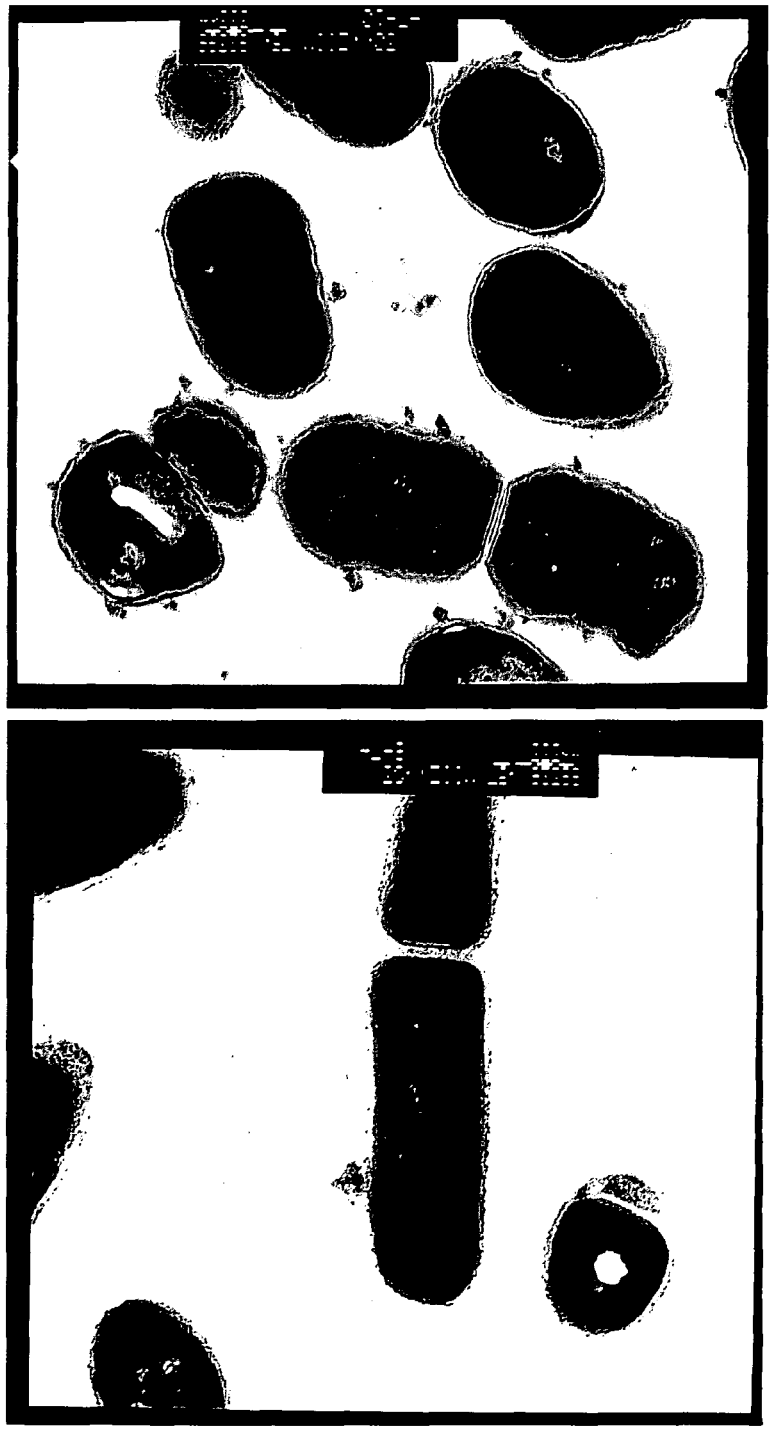

FIG. 4. Is a visualization of MCS using transmission electron microscopy (TEM). Strain DSM 17938 (A) and MM4-1A (B) were grown in MRS. Strain DSM 17938 (A) and MM4-1A (B) were grown in MRS with added vitamin B12 (1 µg/ml) and 200 mM 1,2-PD. White arrowheads indicate MCS formed within the bacteria.

Figure 5A:
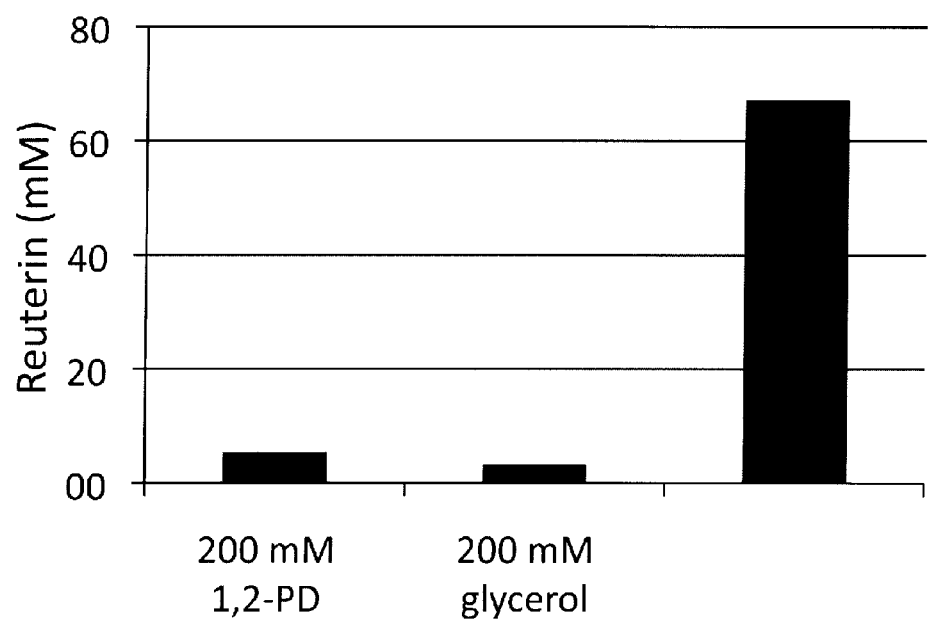

FIG. 5a. Illustrates the effect of reuterin levels in supernatant of MM4-1A cells after exposure to a 200 mM glycerol water solution for 45 min. The bacteria were grown in B12-media (50 ng/ml cobalt) with addition of 200 mM 1,2-PD, 200 mM glycerol or nothing.

Figure 5B:
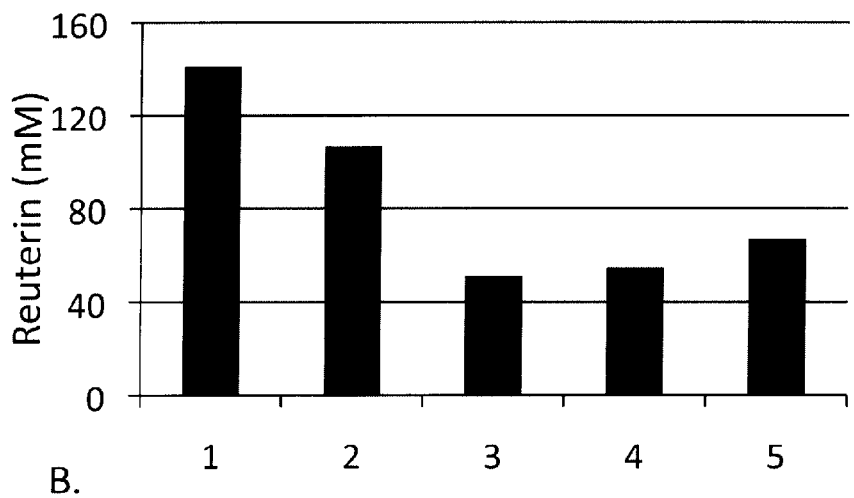
Figure 5B:
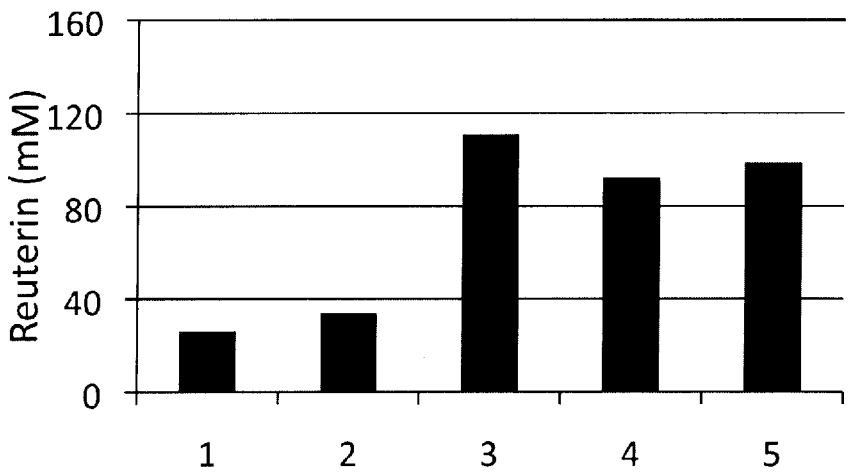

FIG. 5b. Illustrates the effect of reuterin levels (top diagram) in supernatant of MM4-1A cells after exposure to a 200 mM glycerol water solution for 45 min. The bottom diagram illustrates the effect of Reuterin levels associated with cell pellets after exposure to a 200 mM glycerol water solution for 45 min. The bacteria were grown in MRS (1), MRS with added vitamin B12 1 µg/ml (2), MRS with added vitamin B12 1 µg/ml and 200 mM 1,2-PD (3), MRS with added vitamin B12 1 µg/ml and 200 mM glycerol (4), and MRS with added vitamin B12 1 µg/ml and 500 mM glycerol.

Figure 6:
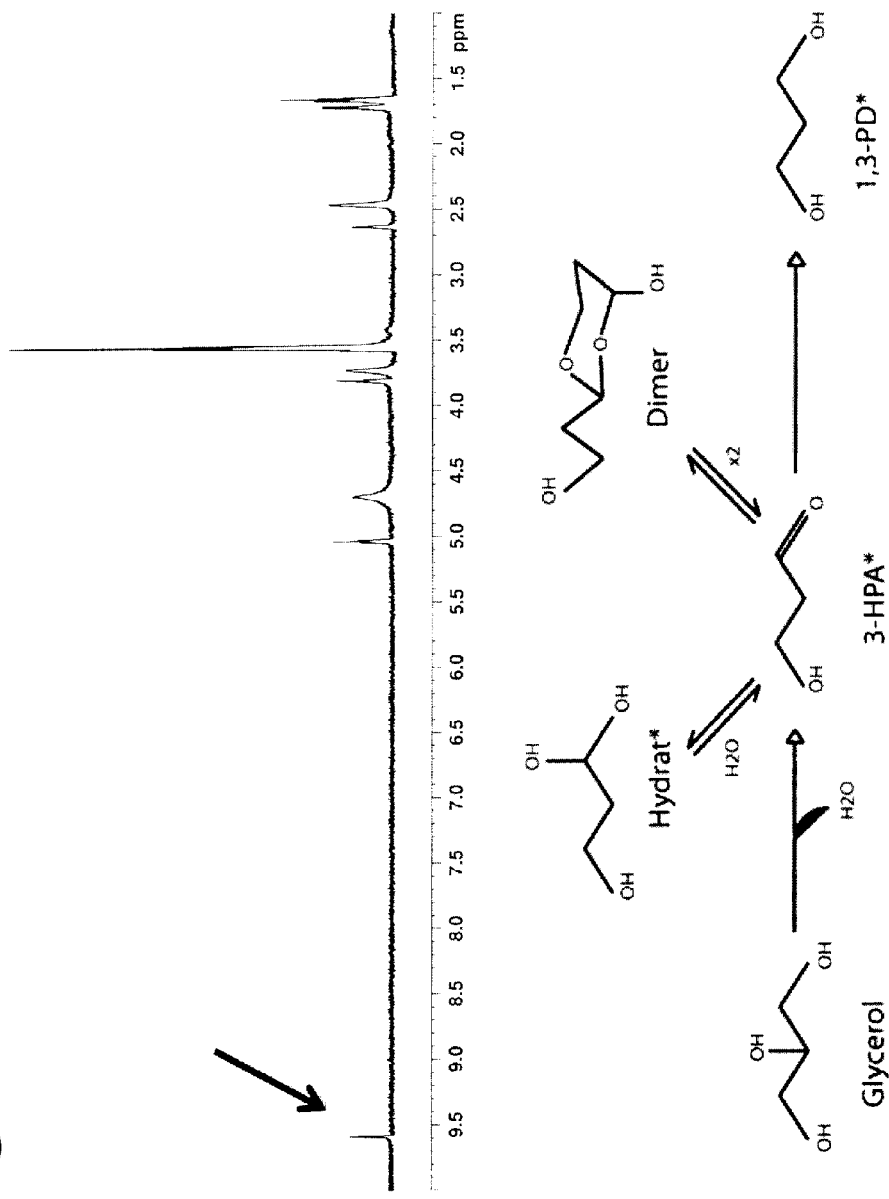

FIG. 6. Is a MAS-NMR micrograph (top) of detected substances associated with MM4-1A cells after the cells had been washed and exposed to a 200 mM glycerol/water solution for 45 minutes. The cells were grown in MRS with addition of 1 µg/ml vitamin B12 and 200 mM glycerol. The arrow points at the aldehyde group in 3-HPA. The bottom illustration shows substances associated with reuterin production. Asterix-marked substances were detected using MAS-NMR.

Figure 7:
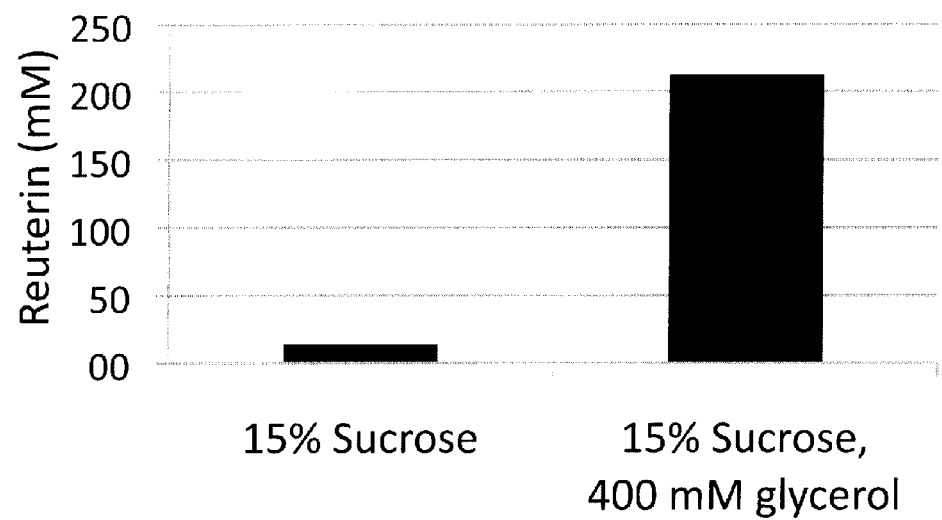

FIG. 7. Is a graph indicating that the presence of sucrose did not interfere with reuterin production.

DETAILED DESCRIPTION OF THE INVENTION

The manufacture of *L. reuteri* cultures to be used as probiotics are cultured in the absence of glycerol and thereafter lyophilized. In those bacteria, the machinery used for reuterin production have not been activated, but under favorable conditions the system can be active 30-60 minutes after the bacteria comes in contact with glycerol. Under non-favorable conditions, this activation can take a much longer time or not occur at all.

In applications where a *L. reuteri* containing product with fast production of reuterin is wanted or where the conditions for growth of *L. reuteri* are non-favorable, the *L. reuteri* culture can be improved by the presence of glycerol during the manufacture of the culture. The glycerol (1-500 mM) can be added during the fermentation step or it can be added together with cryo-protectants at the step after fermentation and possible washing, but before freeze-drying. The reuterin production machinery including the formation of microcompartments of *L. reuteri* can be improved by priming the reuterin producing machinery with 1.2 PD or glycerol at the start of the fermentation.

The cell-culture product can be manufactured in several ways, including but not limited to the three different ways below:

1. The freeze-dried product containing *L. reuteri* cells is allowed to convert glycerol into reuterin at the end of the fermentation step of the manufacturing process but before the freeze-drying step. A product prepared in this way will contain freeze-dried cells and reuterin both within and surrounding the cells. With this manufacture design the freeze-dried bacteria are loaded with reuterin.

2. Like 1 but the reuterin-production machinery of the bacteria is primed with 1.2 PD or glycerol and possibly cobalt or vitamin B-12 at the start of the fermentation step. With this manufacture design the freeze-dried bacteria are loaded with both reuterin and are primed with the capacity to make and store reuterin.

3. The freeze-dried product containing *L. reuteri* cells is allowed to convert glycerol into reuterin after the fermentation and possible washing step, with the addition of glycerol and then allowing for the reuterin production around 30-45 minutes at 37° C. prior to the freeze-drying step. The addition of glycerol for the formation of reuterin can for example be made together with the cryo-protectants. The reuterin-production machinery of the bacteria is primed with 1.2 PD or glycerol at the start of the fermentation step. Advantages of the manufacturing design 3 in relation to way 2 are that way 3 is better suited to be used in many industrial manufacturing set-ups and may allow for better control of the reuterin formation.

Addition of 1,2-PD or glycerol to the growth media has effects both on survival and MCS formation. The enzyme complex PduCDE responsible for the conversion of 1,2-PD into propionaldehyde, are also responsible for the conversion of glycerol into reuterin, which opens the possibility that the MCS formed when bacteria are grown in the presence of 1,2-PD can also work as factories for production of reuterin if the bacteria come in contact with glycerol and lacks means for further metabolism of reuterin (i.e. the bacteria are in stationary phase or are exposed to glycerol in a water solution). The reuterin formed in the MCS are retained within the cell in a higher amount compared to a cell that lacks MCS. This enables the bacteria to be "loaded" with reuterin prior to i.e. freeze-drying.

We repeated what Sriramulu et al observed for the DSM 20016 strain with our MM4-1A and DSM 17938 strains. However, growth in a modified MRS-media, with 65 mM 1,2-PD and low amounts of glucose, is not applicable in an industrial setting due to the very low growth rate of the bacteria in this media. We instead added 200 mM 1,2-PD and 1 ug/ml of vitamin B12 to unmodified MRS-media and tested if the bacteria produced visible MCS after growth for 24 h in 37° C. (using electron microscopy for visualization). Both the MM4-1A and the DSM 17938 strains produced MCS under these conditions (FIG. 4).

Similarly to 1,2-PD, glycerol is metabolised by the same enzyme complex called PduCDE, thus it is possible to also use glycerol to induce the formation of MCS within the bacteria, likewise to what's observed for 1,2-PD. Growth of MM4-1A strain in either 200 mM glycerol or 1,2-PD, produce cells that behave in the same way when it comes to reuterin-formation and its association to the bacterial cell pellet, after that the bacteria have been exposed to glycerol in a water solution under 1 h (FIGS. 5a & 5b)

In addition to washing the pellets (see above, FIG. 5b) we also tested a washed cell pellet for reuterin content using MAS-NMR. The MM4-1A strain was then grown into stationary-phase in MRS-media with added B12 (1 ug/l) and 200 mM 1,2-PD. After growth the bacteria were exposed to 200 mM of glycerol in a water solution and incubated for 1 h in 37° C. Cells were kept on ice and washed 2 times in deuterium water (D2O) containing 200 mM glycerol. The pellet (approximately 20 µl wet weight) from the final step were dissolved in 20 µl D2O without glycerol and measured for reuterin content using MAS-NMR. We could detect two out of three forms of reuterin using this method and some degradation products from reuterin and 1,2-PD (FIGS. 6a & 6b).

Apart from priming with Glycerol and 1,2-PD, addition of certain other substances to the growth media showed to have effects on survival of cells, formation of MCS, production of reuterin and fitness of the bacteria, those substances are for example Vitamin B12, cobalt and Vitamin C.

In order to show that addition of vitamin B12 or cobalt to growth media has an impact on fitness of L. reuteri two different types of growth media were studied, MRS (Oxoid) and B12 assay media (Fluka), in relation to reuterin production and fitness of the L. reuteri strains DSM 17938 and MM4-1A. The main difference between these two growth media is that MRS contains an undefined composition of vitamins added in the form of yeast extract, whereas the B12 assay media (hereafter called B12-media) has a defined composition of all vitamins the bacteria need to function properly with the exception of B12, which it lack all together. Most noteworthy when it comes vitamin-composition differences between these two media, is that B12-media consist of 4 g/l vitamin C, probably several magnitudes more then MRS.

We used the B12-media as a tool to monitor reuterin, microcompartment (MCS) formation and fitness of the bacteria in relation to addition of vitamin B12 or cobalt. Vitamin B12 is an essential component for the enzyme complex PduCDE that is responsible for the transformation of glycerol into reuterin. In order for the vitamin B12 molecule to have a biological function it requires a cobalt ion. If cobalt is present in the media but not vitamin B12, reuterin can only be formed if genes of the cob-operon are expressed, as they are essential for the formation of the cobalt containing B12 molecule. As expression of the cob-operon is connected to the expression of the upstream pdu-operon probably via the regulator PocR (Santos F, Vera J L, van der Heijden R, Valdez G, de Vos W M, Sesma F, Hugenholtz J: The complete coenzyme B12 biosynthesis gene cluster of Lactobacillus reuteri CRL1098. Microbiology 2008, 154(Pt 1):81-93; Cheng S, Liu Y, Crowley C S, Yeates T O, Bobik T A: Bacterial microcompartments: their properties and paradoxes. Bioessays 2008, 30(11-12):1084-1095), we tested reuterin production and fitness in relation to addition of vitamin B12 or cobalt to MRS or B12-media.

Both of the strains (DSM 17938 and MM4-1A) were strongly affected considering their reuterin production when cultivated in the B12-media with varying amounts of either vitamin B12 or cobalt (FIG. 1). This is logical as no reuterin production can occur without functioning B12 molecules, which either has to be added directly or synthesized by the bacteria in presence of cobalt ions.

Opposed to B12-media, MRS media already contain an undefined amount of vitamin B12, as the added yeast extract contains a mixture of vitamins. The measured reuterin production from MM4-1A and DSM 17938 cultivated in plain MRS media coincided with what has been earlier reported in the litterateur where the MM4-1A would not reach the same level of reuterin production as the DSM 17938 strain (FIG. 2)(Spinler J K, Taweechotipatr M, Rognerud C L, Ou C N, Tumwasorn S, Versalovic J: Human-derived probiotic Lactobacillus reuteri demonstrate antimicrobial activities targeting diverse enteric bacterial pathogens. Anaerobe 2008, 14(3): 166-171). Opposed to B12-media, addition of vitamin B12 or cobalt to MRS media did not give conclusive results regarding the increase of reuterin production from MM4-1A and DSM 17938.

However, addition of vitamin B12 to MRS-media has a synergistic effect together with 1,2-propenediol (1,2-PD) when it comes to the fitness of the MM4-1A bacteria (FIG. 3). The increase in fitness of the MM4-1A strain when it is cultivated in MRS with added vitamin B12 and 200 mM 1,2-PD correlated with a decrease in detectable reuterin in the media surrounding the bacteria (FIG. 3). We suspected that this phenomenon might be due to that addition of vitamin B12 and 1,2-PD to MRS increased the occurrence of microcompartments (MCS) within the bacteria. The increased occurrence of MCS would cause the produced reuterin to be retained within the formed MCS harboured by the bacteria.

To sum up we have shown that addition of B12 vitamin and 1,2-PD to normal MRS:

Creates visible MCS in both MM4-1A and DSM 17938 (FIG. 4) Increase the resistance towards produced reuterin for MM4-1A grown in MRS with added vitamin B12 (1 ug/l) and 200 mM 1,2-PD (FIG. 3).—Increase the resistance towards produced reuterin for DSM 17938 grown in B12-media with added vitamin B12 (1 ug/l) and 200 mM 1,2-PD (FIG. 3b).

We also showed that the MM4-1A bacteria grown in this way (or with added glycerol instead of 1,2-PD), retain an higher amount of reuterin within the bacterial cell body and a lower amount outside (FIG. 5b)

Addition of vitamin B12 to MRS supplemented with 1,2-PD has an effect when it comes to increasing the ability of MM4-1A to withstand endogenously produced reuterin. A saturation of the growth media with vitamin B12 helps the bacteria to form functioning MCS when grown in the presence of 1,2-PD (FIGS. 3 & 3b).

The preserved L. reuteri loaded with activated microcompartments containing reuterin can be formulated into various compositions, typically creams, lotions, pastes, powders, capsules, tablets, ointments, emulsions, nasal sprays and the like. Such formulations can be prepared by known means, using pharmaceutically acceptable carriers, excipient, solvents or adjutants. Such procedures and ingredients are well known and amply described in standard texts and manuals.

The bacteria according to the invention can be used for preparing compositions intended for example for the prophylaxis or the treatment of disorders linked to pathogens of the cutaneous system, such as Staphylococcus aureus, Streptococcus pyogenes, Propionibacterium acnes, or yeasts. These skin disorders can be in particular atopic dermatitis acne, candidiases, impetigo or eczematous secondary infection. The skin disorders can also be of non-bacterial cause for example rosacea, psoriasis, wounds from burn injuries, bedsores and other slow-healing wounds.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

EXAMPLES

Example 1

Manufacture of Freeze Dried L. reuteri Powder, with Loaded Microcompartments Containing Reuterin Activated During the Fermentation Step Fermentation Media Composition
Dextrose mono hydrate 60 g/l
Yeast extract KAV 20 g/l
Peptone Type PS (of pig origin) 20 g/l
Di ammonium hydrogen citrate 5 g/l
Sodium acetate (x 3 $H_2O$) 4.7 g/l
Di potassium hydrogen phosphate 2 g/l
Tween80 0.5 g/l
Silibione (anti foam) 0.14 g/l
Magnesium sulphate 0.10 g/l
Manganese sulphate 0.03 g/l
Zinc sulphate hepta hydrate 0.01 g/l Water q.s.

Centrifuge Media

Peptone O-24 Orthana (of pig origin)

Cryoprotectants

Lactose (of bovine origin) 33%

Gelatin hydrolysate (of bovine origin) 22%

Sodium glutamate 22%

Maltodextrin 11%

Ascorbic acid 11%

Production steps of freeze dried *Lactobacillus reuteri* powder

Twenty ml of the media is inoculated with 0.6 ml of freeze-dried *Lactobacillus reuteri* powder from a working cell bank vial. The fermentation is performed in a bottle at 37° C. for 18-20 hours without stirring or pH control i.e. statical.

Two 1-liter flasks of the media are inoculated with 9 ml cell slurry per liter. The fermentation is performed at 37° C. for 20-22 hours without stirring or pH control i.e. statical.

The two one liter cell slurries from step no. 2 inoculates the 600-liter vessel. The fermentation is performed at 37° C. for 13 hours with stirring and pH control. At the start of the fermentation the pH is 6.5. The pH control starts when the pH drops below 5.4 using a 20% sodium hydroxide solution. The pH control is set to pH 5.5.

The fourth and final fermentation step is performed in a 15000-liter vessel with the inoculation from step no 3. The fermentation is performed at 37° C. for 9 to 12 hours with stirring and pH control. At the start of the fermentation the pH is 6.5. The pH control starts when the pH drops below 5.4 using a 20% sodium hydroxide solution. The pH control is set to pH 5.5. 100 mM glycerol is added in the final phase of the fermentation, just before the culture reaches the stationary phase. The fermentation is complete when the culture reaches the stationary phase, which can be seen by the reduction of the addition of the sodium hydroxide solution. Roughly 930 liters of the sodium hydroxide solution is added to the 10200 liters of media and 600 liters of inoculum during the fermentation.

The cell slurry from the final fermentation is separated at 10° C. twice in a continuous centrifuge from Alfa Laval. After the first centrifugation the volume of the cell slurry is reduced from roughly 11730 liters to 1200 liters. This volume is washed with 1200 liters of a peptone (Peptone 0-24, Orthana) solution in a 3000-liter vessel and is separated again before the mixing with the cryoprotectants. The washing step with peptone is performed to avoid any freezing-point reduction in the freeze-drying process. After the second centrifugation the volume of the cell slurry is reduced to 495 liters. This volume is mixed with 156 kg of the cryoprotectant solution to reach roughly 650 liters of the cell slurry.

The cell slurry is pumped to a 1000-liter vessel. The vessel is then transported to the freeze-drying plant. At the freeze-drying plant, exactly 2 liters of the cell slurry is poured on each plate in the freeze dryer. The maximum capacity of the freeze dryer is 600 liters and all excessive cell slurry volume is thrown away. The cell slurry of *Lactobacillus reuteri* has a dry matter content of 18% and is freeze dried for four to five days. During the freeze-drying process, the pressure in the process is between 0.176 mbar and 0.42 mbar. The vacuum pump is started when the pressure reaches 0.42 mbar. The PRT (pressurizing test) is used to determine when the process is complete. If the PRT or the increase of pressure is less then 0.02 mbar after 120 seconds, the process is stopped.

Example 2

Manufacture of Freeze Dried *L. reuteri* Powder, with Loaded Microcompartments Containing Reuterin Primed and Activated During the Fermentation Step Production process like in EXAMPLE 1 but primed with additional 200 mM 1,2-PD, vitamin C (4 g/l) and of vitamin B12 (1 ug/ml) in the growth media.

Example 3

Manufacture of Freeze Dried *L. reuteri* Powder, with Loaded Microcompartments Containing Reuterin, Primed During the Fermentation Step and Activated for Reuterin Formation Before the Freeze-Drying Step Production process like in EXAMPLE 1 but primed with additional 200 mM 1,2-PD, vitamin C (4 g/l) and vitamin B12 (1 ug/ml) to the growth media. But without 100 mM glycerol added in the fermentation phase but instead added to the cell slurry before transported to the freeze-drying plant.

Example 4

Preparation of Ointment with *L. reuteri*, with Activated Reuterin Production Machinery An Ointment is Prepared from the Following Components:

Freeze-dried powder of *L. reuteri*, with activated reuterin-production machinery using for example any of the manufacturing methods described above.

Excipients for the product (water-free oil stabilized with solid fat or wax) Oil, preferably a vegetable oil, for example rapeseed- or palm-oil, solid fat, for example beeswax, preservatives and stabilizers, any known in the art of ointments.

The process will include a melting of the solid part, and mixing with the oil (AkomedR, AAK) and the other ingredients. The Freeze-dried powder *L. reuteri* is added into the mix at a temperature below 55° C. The mixture is stirred until it is solidified to give an ointment.

The ointment will be filled in tubes, and sealed. The resulting ointment contains approximately 10E+08 CFU of the prepared *L. reuteri* culture per gram of ointment.

Example 5

Treatment of Rosacea in a Human Subject

A female subject with a long history of rosacea, is treated with freeze-dried *L. reuteri* cultures manufactured according to the invention herein. The subject is treated twice daily, in the morning and at night. A thin layer of ointment is rubbed into the skin on each occasion.

After 2 weeks, the rosacea is visibly improved in absence of antibiotics, which were prescribed for the treatment of the condition. On cessation of *L. reuteri* treatment the condition returns but is suppressed with regular administration of *L. reuteri*.

Example 6

Nasal Spray Preparation

A nasal preparation comprised of *L. reuteri*, loaded with microcompartment structures that are ready to be used for reuterin production, can take a variety of forms for administration, for example spray, drops, gel, ointment, cream, powder or suspension, using a dispenser or other device as needed. A variety of dispensers and delivery vehicles are known in the art, including single-dose ampules, atomizers, nebulizers, pumps, nasal pads, nasal sponges, nasal capsules, and the like.

More generally, the preparation can take a solid, semi-solid, or liquid form. In the case of a solid form, the components may be mixed together by blending, tumble mixing, freeze-drying, solvent evaporation, co-grinding, spray-drying, and other techniques known in the art.

A semi-solid preparation suitable for intranasal administration can take the form of an oil-based gel or ointment.

In a preferred embodiment, the nasal preparation is in liquid form, which can include an oil solution, an oil suspension. The liquid preparation is administered as a nasal spray or as nasal drops, using devices known in the art, including nebulizers capable of delivering selected volumes of formulations as liquid-droplet aerosols. For example, a commercially available spray pump with a delivery volume of 50 µl or 100 µL is available from, for example, Valois (Congers, N.Y.) with spray tips in adult size and pediatric size.

The liquid preparation can be produced by known procedures. For example, preparation for nasal administration can be produced by mixing L. reuteri loaded with reuterin, in an oleaginous base, such as a pharmaceutically-acceptable oil like olive oil, lanoline, silicone oil, glycerine fatty acids, and the like.

It will be appreciated that excipients necessary for formulation, stability, and/or bioavailability can be included in the preparation. Exemplary excipients include sugars (glucose, sorbitol, mannitol, sucrose), uptake enhancers (chitosan), thickening agents and stability enhancers (celluloses, polyvinyl pyrrolidone, starch, etc.), buffers, preservatives, and/or acids and bases to adjust the pH, and the like.

Although the invention has been described with reference to specific examples, it will be appreciated by those skilled in the art that the invention may be embodied in many other forms.

What is claimed is:

1. A method for producing freeze-dried *Lactobacillus reuteri* cells having reuterin retained inside the cells, comprising:
    growing cells of a *Lactobacillus reuteri* in a fermentation step;
    adding a priming substance selected from the group consisting of glycerol and 1,2-propanediol to the cells of the *Lactobacillus reuteri* at the start of the fermentation step so that the *Lactobacillus reuteri* cells form microcompartments and produce reuterin therein;
    adding glycerol at the end of the fermentation step to the *Lactobacillus reuteri* cells to further produce reuterin by the *Lactobacillus reuteri* cells;
    freeze-drying the cells of the *Lactobacillus reuteri* containing microcompartments and reuterin in the cells; and
    storing the freeze-dried culture of *Lactobacillus reuteri* cells;
    wherein the microcompartments enable the reuterin to be retained inside the freeze-dried cells of *Lactobacillus reuteri* during storage in an amount greater than in cells lacking microcompartments.

2. The method of claim 1 further comprising washing the cells and freeze-drying the cells after fermenting.

3. The method of claim 2 wherein the step of washing the cells after the fermenting step further comprises adding at least one cryo-protectant together with the glycerol after the fermenting step and the washing process, and before the freeze-drying.

4. The method of claim 2 wherein the freeze-drying takes place about 30-45 minutes after reuterin production has begun.

5. The method of claim 1 further comprising adding at least one cryo-protectant to the cells.

6. The method of claim 1, wherein the fermenting step comprises adding at least one of cobalt or vitamin B-12 to the cells at the beginning of the fermenting step.

7. The method of claim 1, wherein the priming substance is glycerol.

8. The method of claim 1, wherein the priming substance is 1,2-propanediol.

9. The method of claim 1, further comprising adding a survival improving substance selected from the group consisting of vitamin B12, cobalt and vitamin C.

10. The method of claim 7, further comprising adding a survival improving substance selected from the group consisting of vitamin B12, cobalt and vitamin C.

11. The method of claim 8, further comprising adding a survival improving substance selected from the group consisting of vitamin B12, cobalt and vitamin C.

12. The method of claim 11, wherein the survival improving substance are vitamin B12 and cobalt.

* * * * *